(12) United States Patent
Enemark

(10) Patent No.: US 10,932,947 B2
(45) Date of Patent: Mar. 2, 2021

(54) MICRO DROP ADAPTER FOR DROPPER BOTTLES

(71) Applicant: Paul Enemark, San Antonio, TX (US)

(72) Inventor: Paul Enemark, San Antonio, TX (US)

(*) Notice: Subject to any disclaimer, the term of this patent is extended or adjusted under 35 U.S.C. 154(b) by 367 days.

(21) Appl. No.: 15/950,300

(22) Filed: Apr. 11, 2018

(65) Prior Publication Data

US 2019/0314193 A1    Oct. 17, 2019

(51) Int. Cl.
*A61F 9/00* (2006.01)
*B65D 47/18* (2006.01)

(52) U.S. Cl.
CPC ............ *A61F 9/0008* (2013.01); *B65D 47/18* (2013.01)

(58) Field of Classification Search
CPC ......... A61F 9/0008; A61F 9/00; B65D 47/18; B65D 47/14; B65D 51/225; B65D 2251/0096; B65D 2401/00; B65D 2251/0025; B65D 1/08
See application file for complete search history.

(56) References Cited

U.S. PATENT DOCUMENTS

| | | |
|---|---|---|
| 3,612,409 A | 10/1971 | Henning |
| 4,471,890 A | 9/1984 | Dougherty |
| 4,605,398 A | 8/1986 | Herrick |
| 4,739,906 A | 4/1988 | LoTurco |
| 5,221,027 A | 6/1993 | Gibilsco |
| 5,226,568 A | 7/1993 | Newton et al. |
| 5,261,572 A | 11/1993 | Strater |
| 5,358,151 A | 10/1994 | Strasenburgh |
| 5,373,972 A | 12/1994 | Bystrom et al. |
| 5,611,788 A | 3/1997 | Marchment |
| 6,105,828 A * | 8/2000 | Kanner .................. B65D 47/18 222/212 |
| 6,197,008 B1 | 3/2001 | Hagele |
| 6,632,202 B1 | 10/2003 | Hagele |
| 7,537,141 B1 | 5/2009 | Robinson |
| 7,563,256 B2 | 7/2009 | Hearne |
| 7,758,553 B2 | 7/2010 | Poisson et al. |

(Continued)

FOREIGN PATENT DOCUMENTS

| | | |
|---|---|---|
| CN | 202236291 U | 5/2012 |
| CN | 104606048 A | 5/2015 |

(Continued)

OTHER PUBLICATIONS

IDROPR, Internet web site, available at https://www.idropr.com/, date of publication unknown.

(Continued)

*Primary Examiner* — Nicholas J. Weiss
*Assistant Examiner* — Alessandro R Del Priore
(74) *Attorney, Agent, or Firm* — Volk & McElroy, LLP; Michael D. Volk, Jr.; Eric A. Hinojosa

(57) ABSTRACT

The invention described herein concerns a micro drop adapter that is adapted to engage with dropper bottles. The micro drop adapter engages with and surrounds the original tip of the bottle. The micro drop adapter comprises at least one inner tube that is urged against the original tip of the bottle forming a seal and a channel in fluid connection with the bottle. The micro drop adapter comprises an adapter tip that dispenses micro drops, which are drops having a volume of less than approximately 50 microliters. The micro drop adapter further comprises a cap.

14 Claims, 9 Drawing Sheets

(56) References Cited

U.S. PATENT DOCUMENTS

| | | | |
|---|---|---|---|
| 7,846,140 | B2 | 12/2010 | Hagele |
| 8,216,195 | B2 * | 7/2012 | Wu .................... B65D 47/061 |
| | | | 604/302 |
| 8,287,505 | B2 | 10/2012 | Pine |
| 8,517,222 | B2 | 8/2013 | Painchaud et al. |
| 2003/0024947 | A1 | 2/2003 | Joshi et al. |
| 2004/0074925 | A1 | 4/2004 | Faurie |
| 2006/0116649 | A1 | 6/2006 | Hagele |
| 2006/0191959 | A1 | 8/2006 | Davies et al. |
| 2007/0051362 | A1 | 3/2007 | Sullivan et al. |
| 2009/0212133 | A1 | 8/2009 | Collins, Jr. |
| 2009/0259204 | A1 | 10/2009 | Galdeti et al. |
| 2009/0272769 | A1 | 11/2009 | Contreras et al. |
| 2013/0134186 | A1 | 5/2013 | Defemme et al. |
| 2015/0038925 | A1 | 2/2015 | Parunak et al. |
| 2019/0224044 | A1 * | 7/2019 | Song .................... A61F 9/0008 |

FOREIGN PATENT DOCUMENTS

| | | |
|---|---|---|
| DK | 2986539 | 8/2018 |
| JP | 07004812 | 2/1995 |
| JP | 2005211184 A | 8/2005 |
| KR | 101675989 B1 | 11/2016 |
| WO | 2014055676 A1 | 4/2014 |
| WO | 2014170736 A1 | 10/2014 |

OTHER PUBLICATIONS

Nanodropper, Internet web site, available at https://web.archive.org/web/20180630003914/https://nanodropper.com/, published on the Internet on Jun. 30, 2018.

* cited by examiner

MICRO DROP ADAPTER FOR DROPPER BOTTLES

CROSS-REFERENCE TO RELATED APPLICATIONS

This application does not claim the benefit of another application.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND

An eye drop bottle typically dispenses about 50 microliters per drop, which is about twice the volume the eye can hold. As early as 1992, certain researchers advocated for the use of a "micro drop" in eye drop bottles. The proposed micro drop would consist of drop volumes of about 16 microliters, since the research indicated that the medicinal efficacy was not affected while patients experienced fewer side effects. For purposes of the present disclosure, a micro drop will be understood to be any drop having less than the typical 50 microliters volume. Additionally, it was found that patients preferred the micro drops. However, to date the use of micro drops has never been adopted by the pharmaceutical companies or bottle manufacturers. There may be various industry pressures or motivations preventing adoption of this technology by the manufacturers considering that if the drop is half the size, then the bottle will last twice as long, potentially resulting in sales volumes and profits being cut in half. However, that may not be true considering that shelf life limits extended or multiple uses of many medicinal drops. Therefore, production costs could be lowered for a company making smaller volume bottles without affecting sales.

Nevertheless, since current bottles do not make use of micro drops, there is a long felt patient need for a more efficient and comfortable drop applicator. Additionally, there are many non-medicinal use instances wherein consumers would find a micro-drop adapter advantageous. Take for example the daily cleaning and conditioning of contact lenses. Contact lens solution can be used more efficiently when dispensed in micro drops. The consumer benefits from the increased economy, and the public benefits from less run-off solution entering the water system.

To address this problem a dropper bottle could be manufactured with a micro-dropper tip. However, since that may or may not occur, consumers desire the option to change the bottle as it is sold or otherwise convert their existing legacy bottles into micro drop dispensing bottles. There have been prior art attempts to achieve this, but those have various failings. Take for example, U.S. Pat. No. 7,563,256 "Cannula Tip Eye Drop Dispenser" which sets out various dropper tips that are intended to replace or be substituted for the original tip that came with the bottle. In one embodiment, the replacement tip has a needle like portion that extends down into the bottle to penetrate the diaphragm barrier (the barrier is used to prevent contamination in certain medications). This is obviously not desirable because it damages and circumvents the purpose of the diaphragm barrier. Furthermore, the downward extending needle prevents the bottle from being completely drained, which defeats the purpose of the more efficient micro-drops. In another embodiment of the same patent, a replacement tip is provided that does not have a needle. However, both this replacement tip and the previously discussed tip pre-suppose that either the bottle had no existing dropper tip or the original tip of the bottle is removable. The modern reality is simply not so. Most liquids (including medicinal and non-medicinal) that are meant to be dispensed via drops are sold in a dropper bottle having a tip. And the tip of many modern day dropper bottles is not removable because it is formed along with the bottle as a monolithic structure. Because of this, the prior art cannot be applied to the majority of dropper bottles consumers experience in the market.

BRIEF SUMMARY

It is a goal of the present invention to provide an adapter that will work with the majority of existing dropper bottles that a consumer will experience in the market of drop dispensable liquids. This adapter will convert a user's existing dropper bottle into a micro drop dispensing bottle. The present invention addresses the need in the form of an adapter that can be attached directly to the user's legacy or existing eye dropper bottle. To accomplish the goal of the present invention, the adapter comprises a coupler to attach to the original bottle, an internal sheath—referred to as the "inner tube"—configured to at least partially surround and make a seal with the tip of the original bottle, a micro drop forming tip that is in fluid connection with the inner tube, and a removable new cap that can engage the adapter to protect the micro drop forming tip and thereby protect the bottle contents from external contamination.

DETAILED DESCRIPTION

Figure 1:
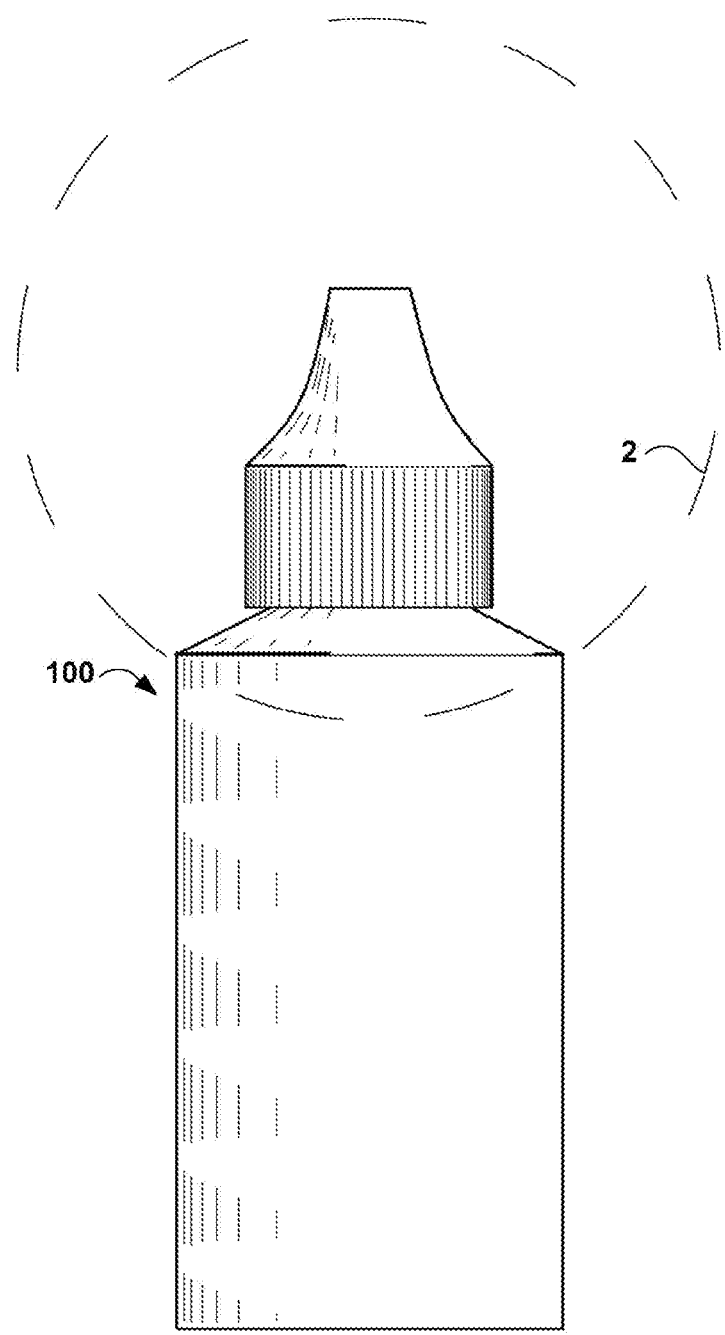
FIG. 1 shows an orthogonal front view of a typical prior art eye dropper bottle with the original lid secured in place.

The micro drop adapter is described herein according to multiple implementations. As a convention for orientation, the descriptive directions of up, above, on top of, down, under, below, etc. may be used. One having ordinary skill in the art will understand that a bottle is typically oriented with the base or bottom of the bottle in the lowest position and the tip of the bottle will be positioned in the highest position. Therefore, terms such as up, above, on top of, etc. will refer to a relative position that is further from the base or bottom of the bottle. And similarly, terms such as down, under, below, etc. will refer to a relative position that is closer to the base or bottom of the bottle.

The typical prior art dropper bottle 100, shortened to "the bottle 100," is well understood in the art, but essentially consists of a circular or oval shaped base, a sidewall, and a top dispensing portion. See FIG. 1-3. The bottle 100 is capable of dispensing drops having approximately 50 microliters in volume. The top dispensing portion of the bottle typically consists of an original drop dispensing tip 104 and a lid 105. See FIG. 2. The original drop dispensing tip 104, shortened to "original tip 104," is typically comprised of a substantially cylindrical threaded portion 106 below a substantially frustoconical cone 107 having a base that tapers to an opening 108 in fluid connection with inside of the bottle 100. The lid 105 engages the threaded portion 106 at the base of the original tip 104 to surround and enclose the original tip 104, thereby creating a seal against the opening 108. FIG. 3 shows a cross sectional view of the typical prior art eye dropper bottle 100 with the lid 105 removed.

The present disclosure describes various implementations of a micro drop adapter that is capable of dispensing micro drops. Some of the below described, implied, or understood implementations are capable of dispensing a micro drop of a particular pre-defined volume. However, certain implementations will dispense a micro drop having a pre-defined average volume in the range of 10-30 microliters.

Figure 2:
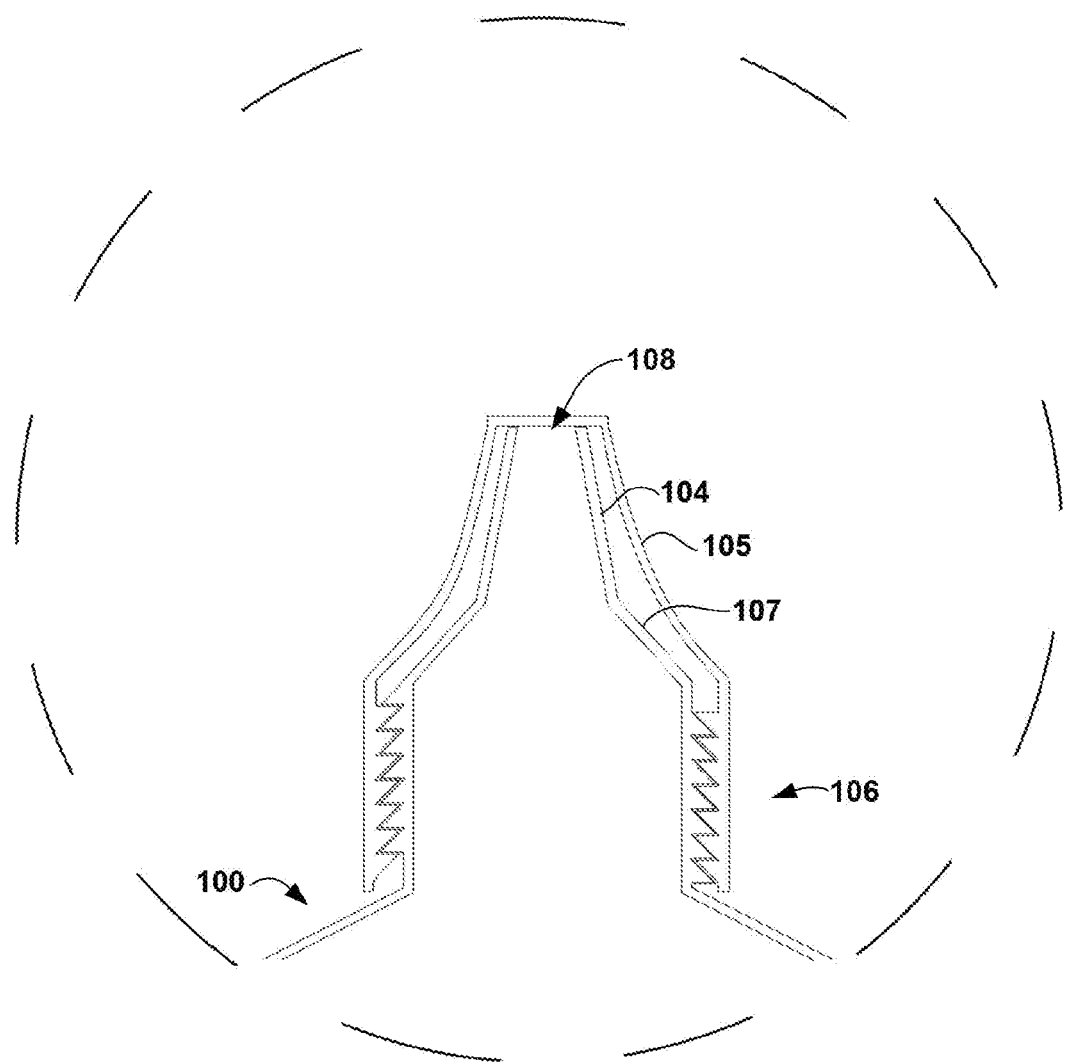
FIG. 2 shows a partial cross sectional view of a typical prior art eye dropper bottle with the original lid secured in place.
Figure 3:
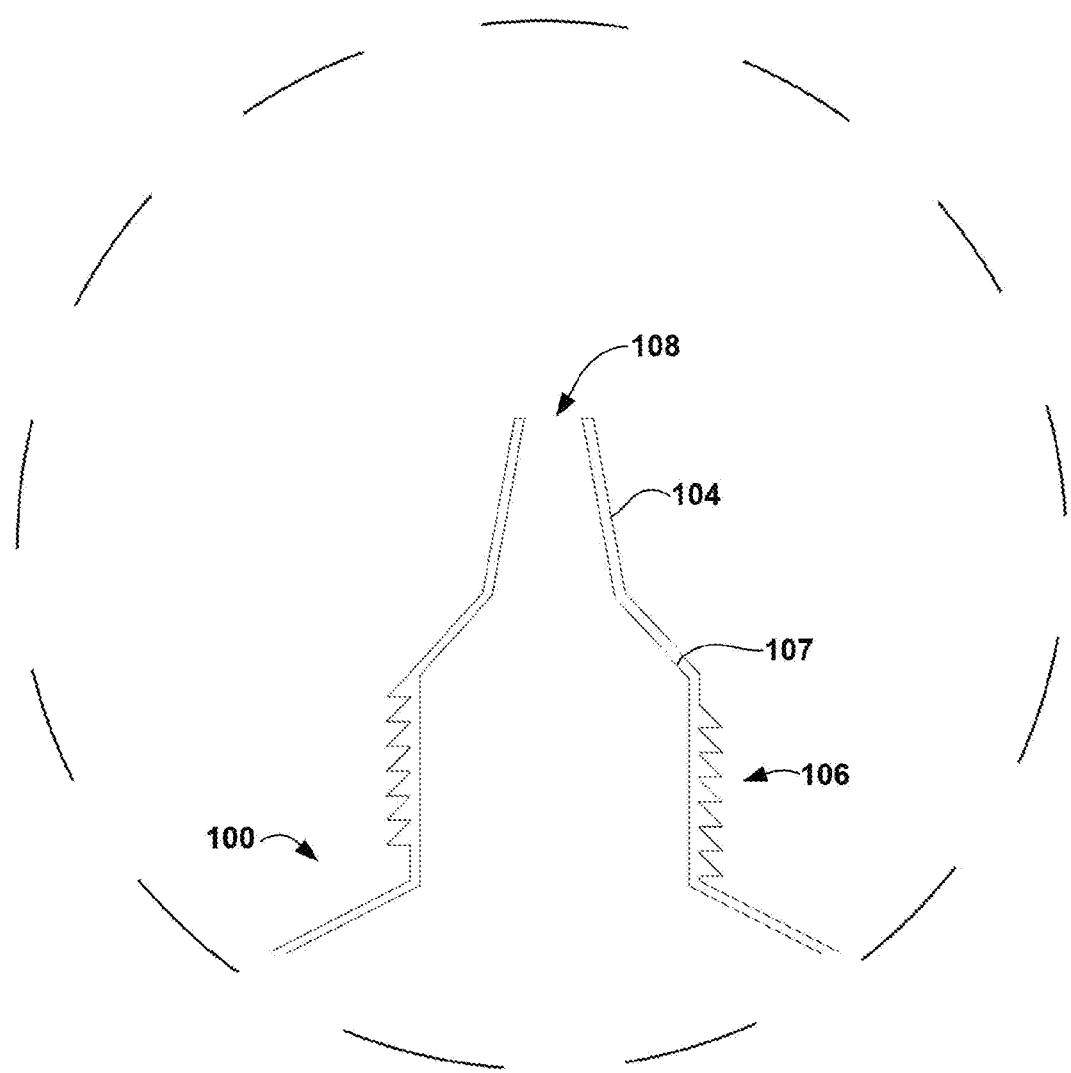
FIG. 3 shows a partial cross sectional view of the typical prior art eye dropper bottle of FIG. 1 with the original lid removed.
Figure 4:
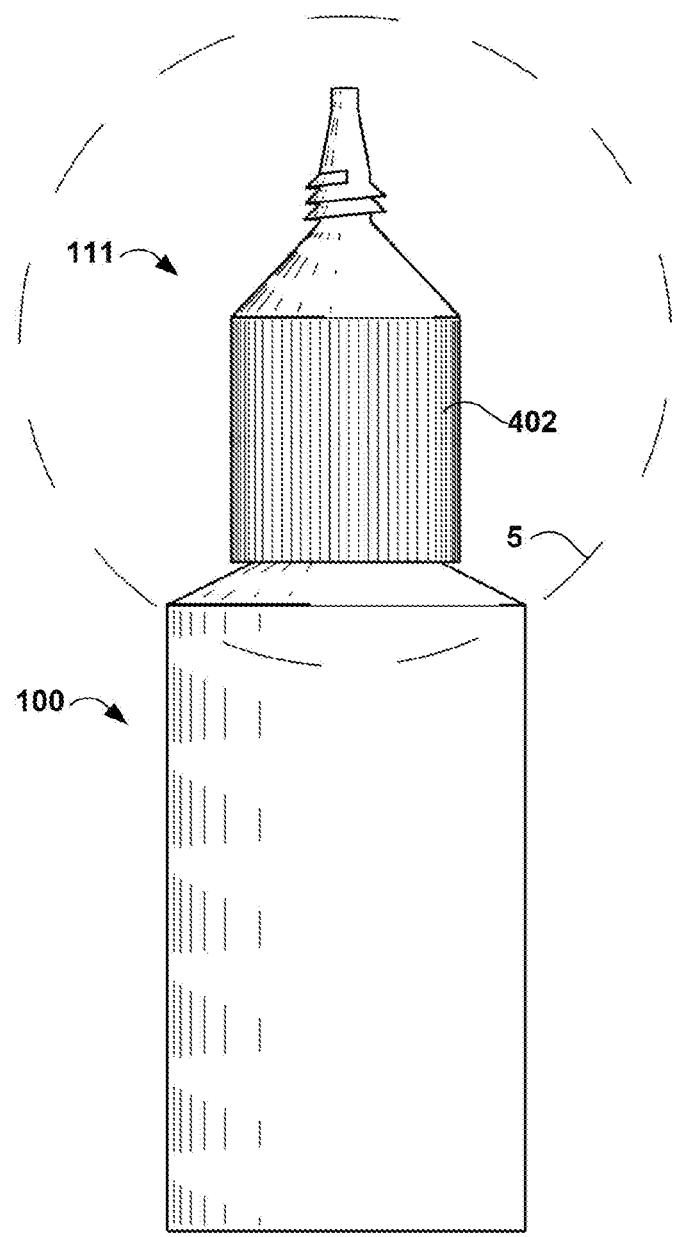
FIG. 4 shows an orthogonal front view of a first implementation of the disclosure secured to the typical prior art eye dropper bottle.

The micro drop adapter 111, shortened to "the adapter 111," of the implementations of FIG. 4-7 is shown in orthogonal and cross sectional views as positioned on the eye dropper bottle 100 of FIG. 1-3. The adapter 111 comprises a substantially cylindrical body section 112, a substantially frustoconical cone section 113, an inner tube 114, and an adapter tip section 115, such that the adapter tip section 115 is connected to the body section 112 via the cone section 113.

The body section 112 of the adapter 111 is tubular with a body outer wall 116, a body inner wall 117, a body top end 118, and a body bottom end 119, wherein the body bottom end 119 has a body opening 120 and the body top end 118 is connected to the widest portion of the cone section 113. The inner wall 117 of the body section 112 is configured to receive and engage the threaded portion 106 of the bottle 100. Therefore, the body section 112 of the adapter 111 comprises a bottle retainer 121 positioned on the body inner wall 117 towards the body bottom end 119. In the implementation shown in FIG. 5, the bottle retainer 121 is comprised of a threaded section to engage with the threaded portion 106 of the bottle 100. Having read the present disclosure, it will be readily apparent to one having ordinary skill in the art that in addition to threads that correspond to the threads of the bottle, there are many other forms and mechanisms the bottle retainer 121 could be comprised of. For example, instead of threads, the bottle retainer 121 could utilize a multitude of fine filaments or bristles, or a deformable ring, or an elastically deformable ring—such that the threaded portion 106 of many different bottles 100 could be engaged without prior knowledge of the particular thread dimensions. In some implementations, the body section further comprises a grip enhancer on the exterior surface. In some implementations the grip enhancer is a multitude of grooves formed into the body outer wall.

The substantially frustoconical cone section 113, or simply the "cone section 113," of the adapter 111 has a cone outer wall 122, a cone inner wall 123, a cone top end 124, and a cone bottom end 125. The cone bottom end 125 is connected to the body top end 118. The cone inner wall 123 of the cone section 113 and the body inner wall 117 of the body section 112 together define a cavity 126. The cavity 126 is capable of accommodating a diverse range of original tip 104 shapes.

In some implementations, the micro drop adapter does not have a cone section 113 but rather the body section 112 creates the cavity 126 with the adapter tip section 115.

Figure 5:
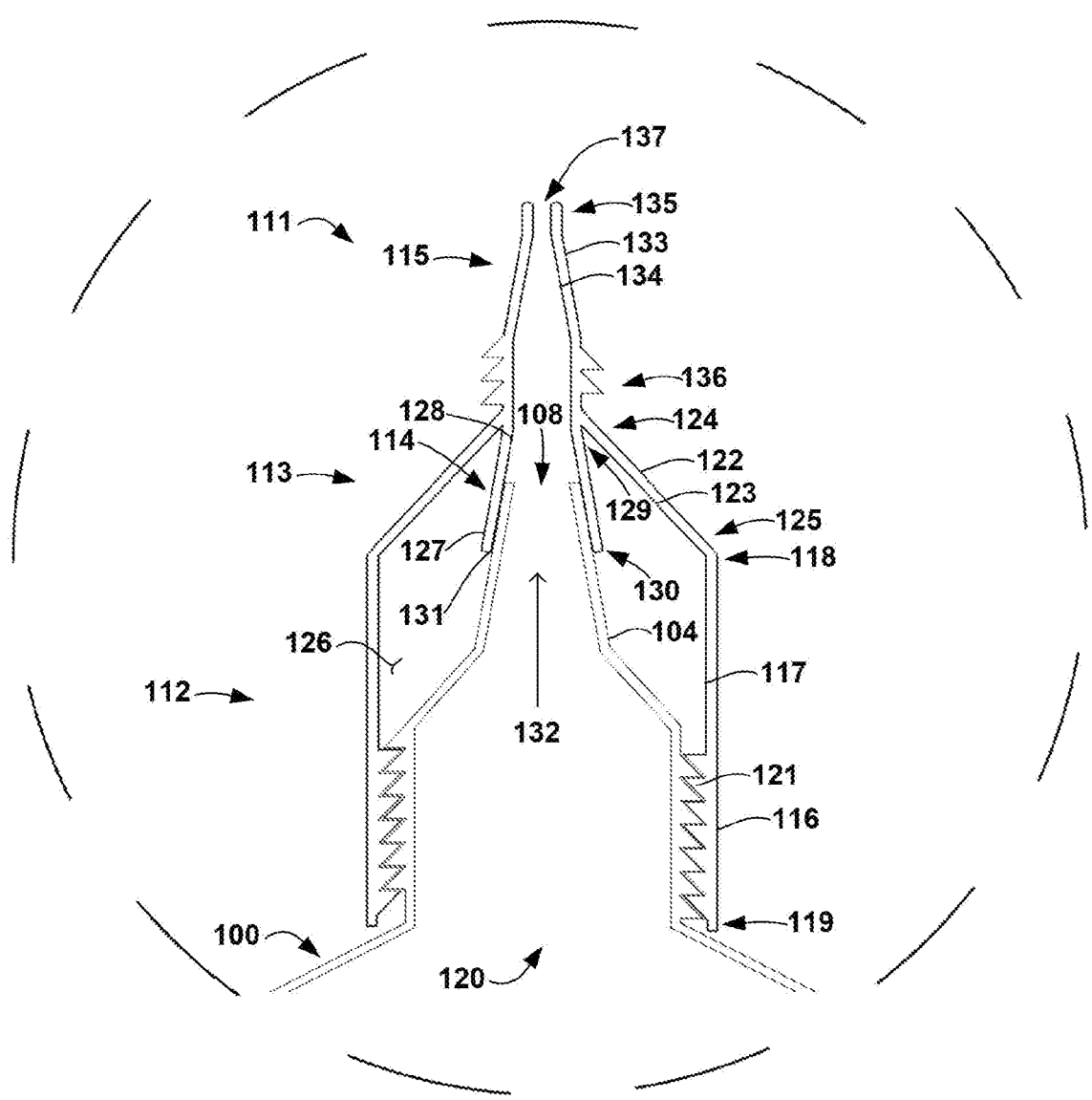
FIG. 5 shows a partial cross sectional view of a first implementation of the disclosure secured to the typical prior art eye dropper bottle.
Figure 6:
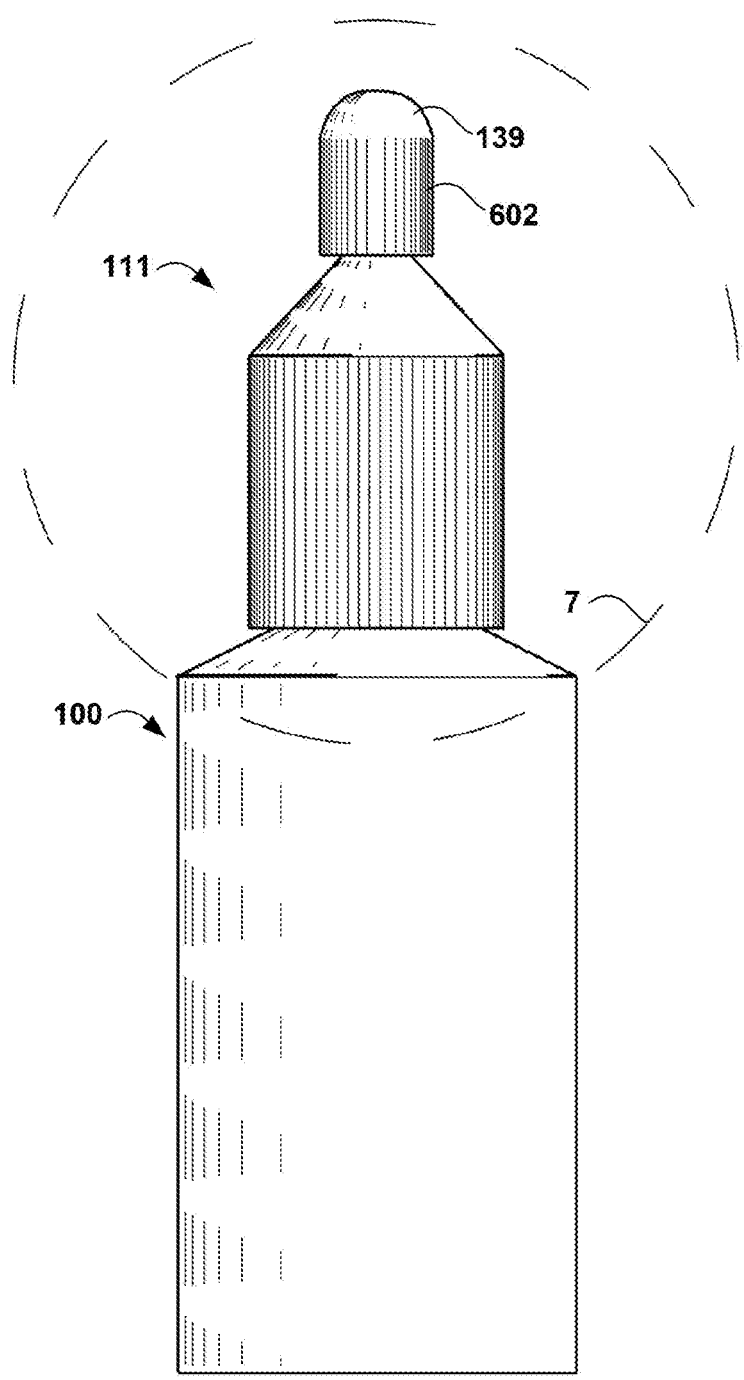
FIG. 6 shows an orthogonal front view of a second implementation of the disclosure secured to the typical prior art eye dropper bottle.

Still referring to FIG. 5, the inner tube 114 comprises an inner tube outer wall 127, an inner tube inner wall 128, an inner tube top end 129, and an inner tube bottom end 130. The inner tube top end 129 is connected to the cone inner wall 123 at the cone top end 124. The inner tube 114 extends downward from the cone top end 124 into the cavity 126. The inner tube bottom end 130 is adapted to contact the original tip 104 of bottle 100 such that at least part of the inner tube inner wall 128 forms a seal 131 against the exterior of original tip 104 of bottle 100 without obstructing opening 108 of bottle 100. Thus, inner tube inner wall 128 forms a channel 132 in fluid connection with opening 108 of bottle 100 and its contents.

In some implementations, inner tube 114 is a cylindrical tube. In other implementations, inner tube 114 is a frustoconical tube. In some implementations, inner tube 114 is made of a material that is at least partially elastically deformable. In some implementations, inner tube 114 is made of one or more of the materials comprising the following group: rubber, rubberized silicone, silicone, and plastic.

Still referring to FIG. 5, the adapter tip section 115 comprises a tip section outer wall 133, a tip section inner wall 134, a tip section top end 135, a tip section bottom end 136, and an adapter tip opening 137. The tip section bottom end 136 is connected to the cone top end 124 and the inner tube top end 129, such that the tip section inner wall 134 continues channel 132 and is in fluid connection with the bottle 100. The adapter tip section 115 extends upward from the cone top end 124. Adapter tip opening 137 is positioned at the tip section top end 135. The adapter tip section 115 is configured to dispense individual micro drops from adapter tip opening 137.

In some implementations, adapter tip section 115 will comprise a narrow tube of cylindrical shape. In other implementations, adapter tip section 115 will comprise a tapered tube shape. Regardless of shape or dimension, the adapter tip section 115 is adapted to form and dispense micro drops.

Figure 7:
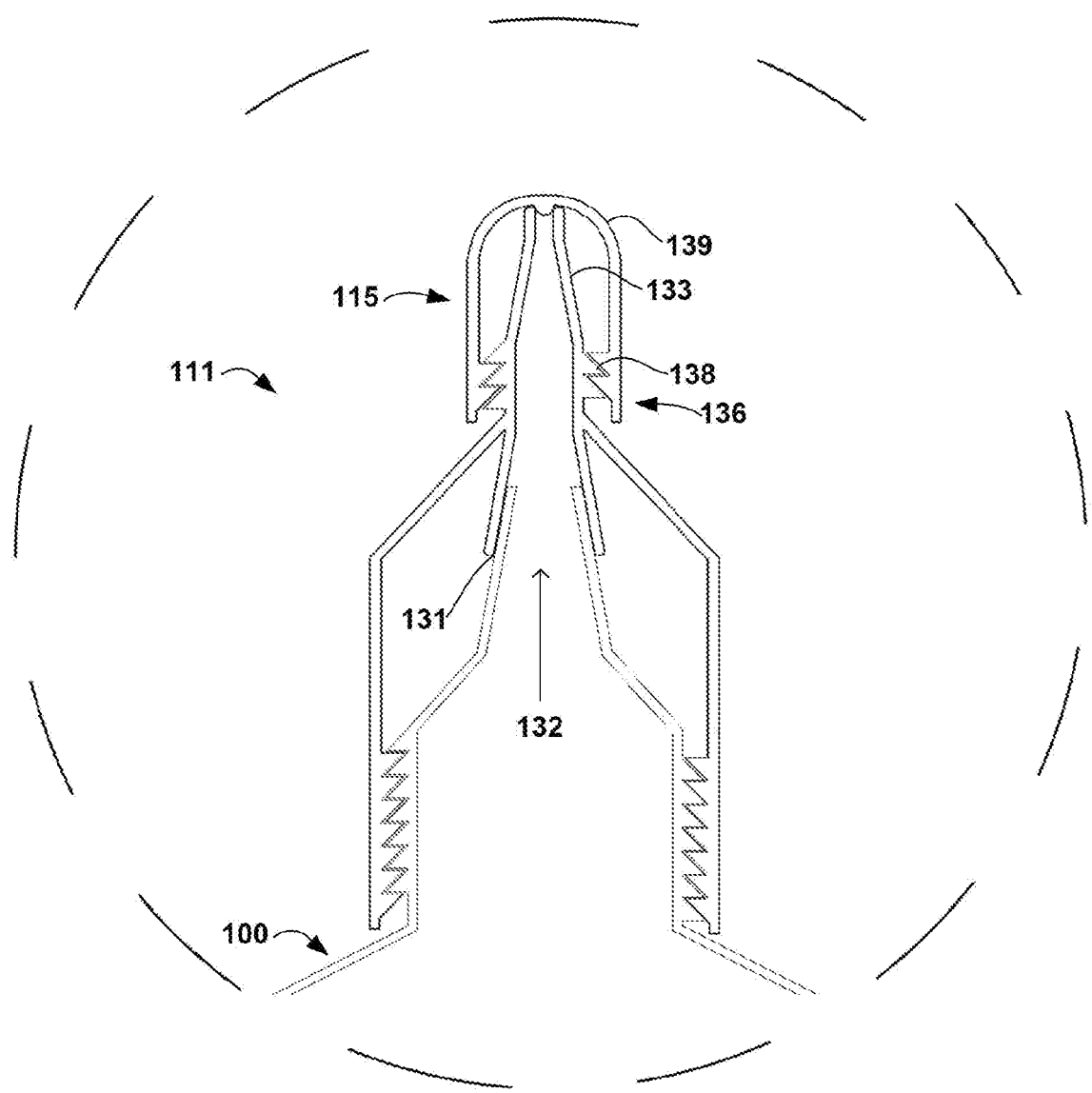
FIG. 7 shows a partial cross sectional view of a second implementation of the disclosure secured to the typical prior art eye dropper bottle.
Figure 8:
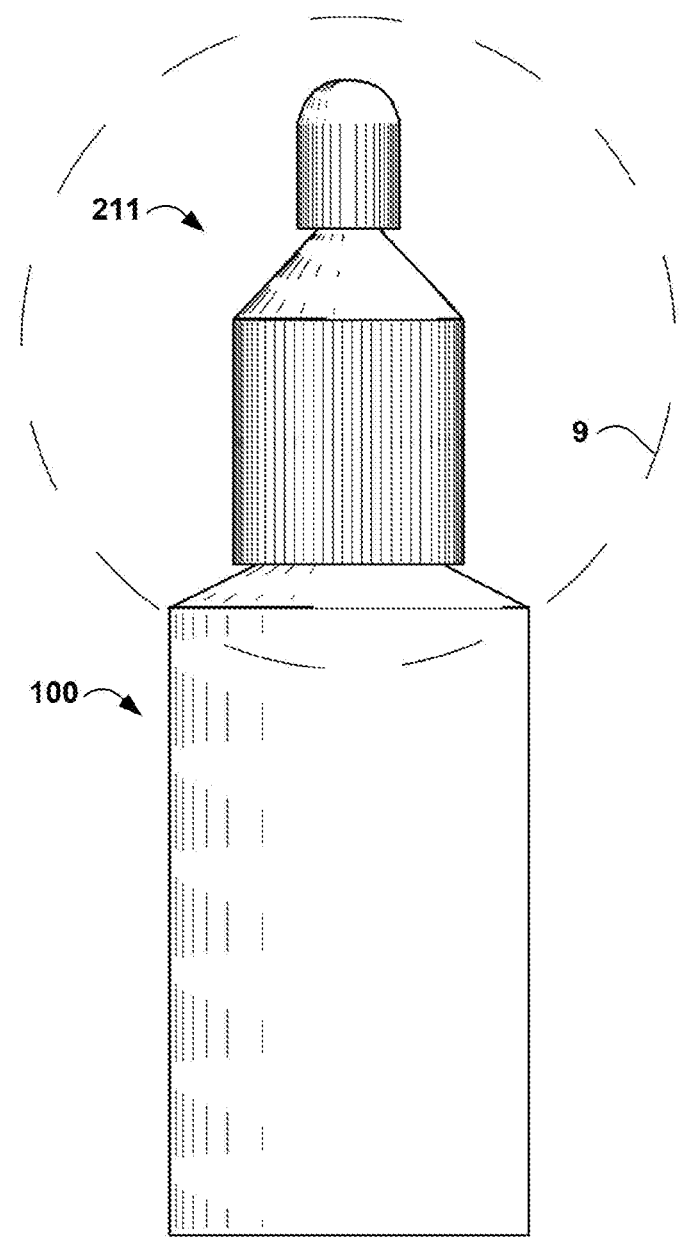
FIG. 8 shows an orthogonal front view of a third implementation of the disclosure secured to the typical prior art eye dropper bottle.

Some implementations will further comprise a cap for the adapter to close off the dispensing channel. Adapter cap 139 will close channel 132 when fully engaged with adapter tip section 115, thus preventing the contents of bottle 100 from being unintentionally dispensed. Referring to the implementation seen in FIG. 7, the tip section outer wall 133 will have a cap retainer 138 positioned towards tip section bottom end 136. The cap retainer 138 will engage adapter cap 139. In FIGS. 5 and 7, the cap retainer 138 is depicted as a threaded section that is engages with the corresponding threaded section of adapter cap 139. However, having read the present disclosure it will be readily apparent to one having ordinary skill in the art that in addition to threads that correspond to the threads of the adapter cap 139, there are many other forms and mechanisms the cap retainer 138 could be comprised of such as a simple lip and groove that retains the adapter cap 139 via an inwardly directed compressive force. Moreover, having read the present disclosure it will be readily apparent to one having ordinary skill in the art that cap retainer 138 could be positioned on the cone section 113 or body section 112 in alternative implementations. In some implementations, the cap adapter further comprises a grip enhancer on the exterior surface. In some implementations the grip enhancer is a multitude of grooves formed into the cap adapter outer wall.

Figure 9:
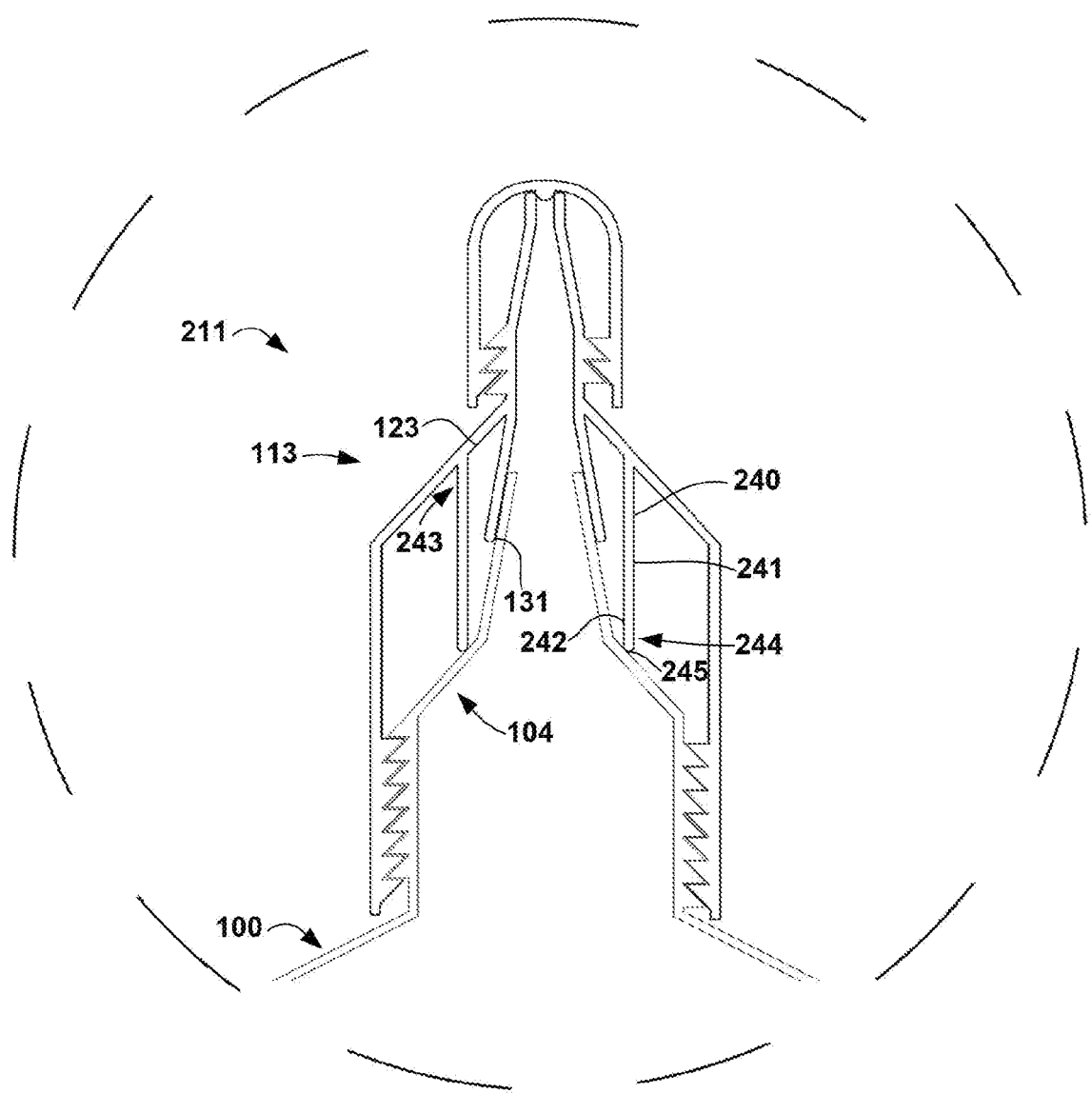
FIG. 9 shows a partial cross sectional view of a third implementation of the disclosure secured to the typical prior art eye dropper bottle.

Turning now to FIG. 9 for reference, some implementations further comprise at least a second inner tube. Adapter 211, shown in FIG. 9, is similar to adapter 111 in many respects. Indeed adapter 211 comprises all of the features and described elements of adapter 111 unless otherwise specified. However, adapter 211 further comprises a second inner tube 240. Second inner tube 240 comprises a second inner tube outer wall 241, a second inner tube inner wall 242, a second inner tube top end 243, and a second inner tube bottom end 244. The purpose of the second inner tube 240 is to create a second seal 245. Second inner tube top end 243 is connected to the cone inner wall 123. The a second inner tube 240 extends down into cavity 126 such that the second inner tube bottom end 244 contacts the exterior of original tip 104. The second seal 245 is created at the point of contact between bottom end 244 and original tip 104. As with the inner tube 114, second inner tube 240 is comprised of rigid materials of construction in some implementations and flexible—resiliently deformable—materials of construction in other implementations.

The adapter 211 seen in FIG. 9 features a second inner tube 240. However, having read the present disclosure it will be understood by one having ordinary skill in the art that an alternative implementation of the presently disclosed adapter could be described as comprising at least one inner tube that creates at least one seal. In other words some embodiments will feature a multitude of inner tubes creating a multitude of seals. The additional seals may be desired in certain adapter implementations for a variety of reasons such as greater resistance to leaking under the applied pressure while dispensing drops, or simply for the purpose of accommodating a larger range of bottle 100 original tip 104 shapes and sizes. The second inner tube 240 of the adapter 211 is also depicted in FIG. 9 as having a larger diameter but being concentric with inner tube 114. This is true in some implementations but one having ordinary skill in the art will appreciate upon reading the present disclosure that this is not a limitation that will apply to all implementations of the present invention.

The adapter implementations have been described as connected sections and functional parts (such as a body section, a cone section, an inner tube section, etc.). That is strictly true of certain implementations. However, having read the present disclosure it will be understood by one having ordinary skill in the art that some implementations will be formed monolithically such that the sections and functional elements are not separate parts that have been connected after the fact—but rather are elements forming a whole unit. In fact, FIGS. 5, 7, and 9 show such implementations.

The adapter of some implementations is constructed from a material that is suitable for sterilization procedures. Some sterilization procedures utilize intense ultraviolet light therefore a suitable material of construction will have the property of being undamaged or highly resilient to exposure to intense ultraviolet light. In plastics, the term is "UV stabilized." Another common sterilization procedure is the use of an autoclave, which involves high pressure and heat. Therefore, other implementations will be constructed of a material that can withstand the pressure and heat of autoclave sterilization.

Although the invention has been described and illustrated with a certain degree of detail or with reference to one or more particular embodiments, it is understood that the present disclosure has been made only by way of example. It should be understood that the invention is not intended to be limited to the particular forms disclosed. Furthermore, the invention is amenable to various modifications and alternative forms. Obvious variations and other various changes in the composition, combination, and arrangement of parts can be utilized to by those skilled in the art without departing from the spirit and scope of the invention, as herein disclosed and claimed.

The invention claimed is:

1. A micro drop adapter for a dropper bottle having an original tip comprising:
   a tubular body section having a body interior adapted to engage the dropper bottle;
   a dropper bottle retainer connected to the tubular body section;
   a micro drop forming tip section connected to the tubular body section;
   a cavity created by the body interior and the micro drop forming tip section;
   an inner tube adapted to engage the original tip of the dropper bottle to create a seal, wherein the inner tube extends into the cavity and is connected to the body interior such that the inner tube and micro drop forming tip section create a channel in fluid connection with the dropper bottle; comprising a second inner tube that surrounds the inner tube and is adapted to engage with the original tip of the dropper bottle to create a second seal.

2. The micro drop adapter of claim 1 further comprising:
   a cap retainer; and
   an adapter cap that engages the cap retainer to close the channel.

3. The micro drop adapter of claim 2 wherein the cap retainer is positioned on the micro drop forming tip section.

4. The micro drop adapter of claim 3 wherein the cap retainer comprises a threaded section that corresponds to a threaded section on the adapter cap.

5. The micro drop adapter of claim 2 further comprising a grip enhancer on the adapter cap.

6. The micro drop adapter of claim 5 wherein the grip enhancer comprises a multitude of grooves formed into the adapter cap.

7. The micro drop adapter of claim 1 further comprising a grip enhancer on the tubular body section.

8. The micro drop adapter of claim 7 wherein the grip enhancer comprises a multitude of grooves formed into the tubular body section.

9. The micro drop adapter of claim 1 further comprising:
   a cone section connecting the tubular body section to the micro drop forming tip section.

10. The micro drop adapter of claim 1 wherein the dropper bottle retainer comprises a threaded section that corresponds to a threaded section on the dropper bottle.

11. The micro drop adapter of claim 1 wherein the inner tube is at least partially elastically deformable.

12. The micro drop adapter of claim 1 wherein the inner tube is frustoconical in shape.

13. The micro drop adapter of claim 1 wherein the material of construction is suitable for sterilization.

14. A micro drop adapter for a dropper bottle having an original tip comprising:
- a tubular body section having a body interior adapted to engage the dropper bottle;
- a dropper bottle retainer connected to the tubular body section;
- a cone section connected to the tubular body section;
- a micro drop forming tip section connected to the cone section;
- a cavity created by the body interior, the cone section, and the micro drop forming tip section;
- an inner tube adapted to engage the original tip of the dropper bottle to create a seal,
- wherein the inner tube extends into the cavity and is connected to the body interior such that the inner tube and micro drop forming tip section create a channel in fluid connection with the dropper bottle;
- comprising a second inner tube that surrounds the inner tube and is adapted to engage with the original tip of the dropper bottle to create a second seal;
- a cap retainer; and
- an adapter cap that engages the cap retainer to close the channel.

* * * * *